(12) United States Patent
Hou et al.

(10) Patent No.: US 8,983,621 B2
(45) Date of Patent: Mar. 17, 2015

(54) FUNCTIONAL ELECTRICAL STIMULATION SYSTEM

(75) Inventors: Zengguang Hou, Beijing (CN); Yixiong Chen, Beijing (CN); Pengfeng Li, Beijing (CN); Min Tan, Beijing (CN); Long Cheng, Beijing (CN); Qingling Li, Beijing (CN); Feng Zhang, Beijing (CN); Jin Hu, Beijing (CN); Long Peng, Beijing (CN); Xinchao Zhang, Beijing (CN)

(73) Assignee: Institute of Automation, Chinese Academy of Sciences, Beijing (CN)

( * ) Notice: Subject to any disclaimer, the term of this patent is extended or adjusted under 35 U.S.C. 154(b) by 0 days.

(21) Appl. No.: 13/994,051

(22) PCT Filed: Jun. 28, 2011

(86) PCT No.: PCT/CN2011/076492
§ 371 (c)(1),
(2), (4) Date: Jun. 13, 2013

(87) PCT Pub. No.: WO2013/000122
PCT Pub. Date: Jan. 3, 2013

(65) Prior Publication Data
US 2014/0100638 A1   Apr. 10, 2014

(51) Int. Cl.
*A61N 1/00* (2006.01)
*A61N 1/378* (2006.01)
*A61N 1/36* (2006.01)

(52) U.S. Cl.
CPC .............. *A61N 1/378* (2013.01); *A61N 1/3782* (2013.01); *A61N 1/36* (2013.01); *A61N 1/36003* (2013.01)
USPC .......................................................... 607/63

(58) Field of Classification Search
USPC ............................ 607/60, 61, 63, 115, 72, 74
See application file for complete search history.

(56) References Cited

U.S. PATENT DOCUMENTS

| 4,510,936 A | 4/1985 | Fourcin |
| 5,514,165 A | 5/1996 | Malaugh |

FOREIGN PATENT DOCUMENTS

| CN | 1272798 A | 11/2000 |
| CN | 101244314 A | 8/2008 |

OTHER PUBLICATIONS

International Search Report and Written Opinion as issued for International Application No. PCT/CN2011/076492, dated Sep. 8, 2011.

*Primary Examiner* — Christopher Koharski
*Assistant Examiner* — Nadia A Mahmood
(74) *Attorney, Agent, or Firm* — Pillsbury Winthrop Shaw Pittman LLP

(57) ABSTRACT

A functional electrical stimulation system having a boost module to raise an output voltage of a primary power to a first preset voltage, an energy storage module, connected to the boost module, configured to store electrical energy of the first preset voltage, a central control unit configured to generate data packets of electrical stimulation parameters, and an electrical stimulation output channel, connected to the energy storage module, configured to receive the data packets of electrical stimulation parameters, analyze the electrical stimulation parameters from the data packets, convert electrical energy stored in the energy storage module to an electrical stimulation pulse corresponding to the electrical stimulation parameters and apply the electrical stimulation pulse to a part of a user. The functional electrical stimulation system can enhance flexibility and autonomy of an electrical stimulation pulse so that the user can select a personalized electrical stimulation pulse type according to his/her actual conditions.

22 Claims, 6 Drawing Sheets

FUNCTIONAL ELECTRICAL STIMULATION SYSTEM

TECHNICAL FIELD

The invention relates to medical appliances, in particular to a functional electrical stimulation (FES) system.

BACKGROUND

An FES therapy uses a low-frequency current to stimulate denervated muscles, making muscle contraction in order to replace or correct functions that organs and limbs have lost. Currently, research and application on FES have been involved in various fields of clinical treatment. In general, an FES device is a portable stimulator with two to four channels.

A diaphragm pacemaker for controlling and regulating a respiratory movement is an FES system. This system is used to cure respiratory muscle paralysis caused by cerebrovascular disease, brain trauma or high-level spinal cord injury. A pair of electrodes is implanted in bilateral phrenic nerves or surface electrodes are placed on the motor point of the phrenic nerve of the bilateral neck. Then the electrodes are connected to a signal receiver fixed on a chest wall. A controller sends a wireless pulse signal and the receiver converts the wireless pulse signal into a low-frequency current, which stimulates the phrenic nerve through the electrodes to cause the diaphragm contraction.

Further, FES has implemented benefits in treatment of voiding dysfunction. Taking urinary incontinence as an example, it causes myasthenia of the urethral sphincter and pelvic floor muscle due to lower motor neuron injury, causing endless urination dripping or urination just because abdominal pressure slightly increases. On clinical uses, FES stimulates the urethral sphincter and pelvic floor muscle to enhance their muscle strength, which can improve the degree of urinary incontinence significantly. Another example is when the sacral cord micturition center injures, the detrusor muscle is paralyzed and urinary retention occurs. Implanted electrodes are usually used in a clinic to stimulate the detrusor muscle, making this muscle contraction in order to overcome the pressure of the urethral sphincter and empty the bladder.

In addition, the FES therapy can used for upper motor neuron injury to complete some functional activities, such as walking, grasping, and coordinated movement, which can accelerate recovery of voluntary control. The upper motor neuron injury may include cerebrovascular disease, brain trauma, spinal cord injury, cerebral palsy, etc. Limb movement is critical to the rehabilitation of these users, especially users with spinal cord injury. A study found that the electrical signal generated by the limb movement, can cause irritation on the spinal cord stump, which achieves the restoration of part of the spinal cord continuity. Some scientists have proposed a FES-assisted treadmill training method, which can restore muscle strength and promote local tissue repair of spinal cord injury.

SUMMARY

Disadvantages of a conventional FES system may include:
1. The system has poor flexibility and autonomy on arrangement and electrical stimulation parameters can't be adjusted according to a user's need, such as frequency and amplitude;
2. Security and reliability are low. If heart beat anomaly and muscle spasm are induced due to the electrical stimulation, the user cannot cut off the electrical stimulation and quickly send an alarm signal; and
3. Only a single operation mode and simple function can be achieved. The system was used as an independent device for outputting the electrical stimulation in accordance with a preset waveform sequence.

Technical Problems to be Solved

A functional electrical stimulation system may be provided to improve flexibility and enhance the security and reliability, so as to avoid danger during normal use.

Technical Solution

In an embodiment of the present invention, there is provided a functional electrical stimulation system comprising: a primary power; a boost module, connected to the primary power, configured to raise an output voltage of the primary power to a first preset voltage; an energy storage module, connected to the boost module, configured to store electrical energy of the first preset voltage; a central control unit configured to generate data packets of electrical stimulation parameters; an electrical stimulation output channel, connected to the energy storage module, configured to receive the data packets of electrical stimulation parameters, analyze the electrical stimulation parameters from the data packet, convert electrical energy stored in the energy storage module to an electrical stimulation pulse corresponding to the electrical stimulation parameters, and apply the electrical stimulation pulse to a diseased part of a user.

In an embodiment, the electrical stimulation output channel comprises: a low-level controller configured to receive the data packets of electrical stimulation parameters from the central control unit, analyze the electrical stimulation parameters from the data packets, and output a positive control signal and a negative control signal corresponding to the electrical stimulation parameters respectively; a constant-current source, connected to the energy storage module, configured to receive the positive control signal and the negative control signal and convert the electrical energy stored in the energy storage module to a bipolar electrical stimulation pulse according to the positive control signal and the negative control signal; a surface electrode having two poles connected to two output ends of the constant-current source respectively, the surface electrode configured to apply the bipolar electrical stimulation pulse to the diseased part of a user. In an embodiment, the constant-current source is a bridge constant-current source, and two poles of the surface electrodes are connected across both ends of a bridge arm of the bridge constant-current source respectively.

In an embodiment, the constant-current source is a bridge constant-current source, comprising a first operational amplifier UA, a second operational amplifier UB, a first resistor R1, a second resistor R2, a third resistor R3, a fourth resistor R4, a fifth resistor R5, a sixth resistor R6, a first transistor Q1, and a second transistor Q2; wherein the first operational amplifier UA, the first resistor R1, the second resistor R2, the third resistor R3 and an equivalent resistance of the user R7 form a constant-current control circuit for a negative pulse; a positive input end of the first operational amplifier UA is connected to a negative control signal generated by the low-level controller to control an amplitude of a negative pulse current; the first resistor R1 is connected to an output end of the first operational amplifier UA and a base of the first transistor Q1; the second resistor R2 is connected to a negative input end of the first operational amplifier UA and an emitter of the first transistor Q1; the third resistor R3 is connected to the emitter of the first transistor Q1 and a ground; a collector of the first transistor Q1 is connected to the output of the boost module via a positive polarity switch. The second operational amplifier UB, the fourth resistor R4, the fifth resistor R5, the sixth resistor R6 and the equivalent resistance of the user R7 form a constant-current control circuit for a positive pulse; a positive input end of the second operational amplifier UB is connected to a positive control signal generated by the low-level controller to control an amplitude of a positive pulse current; the fourth resistor R4 is connected to an output end of the second operational amplifier UB and a base of the second transistor Q2; the fifth resistor R5 is connected to a negative input end of the second operational amplifier UB and an emitter of the second transistor Q2; the sixth resistor R6 is connected to the emitter of the second transistor Q2 and the ground; a collector of the second transistor Q2 is connected to the output of the boost module via the negative polarity switch. The constant-current control circuit for the negative pulse and the constant-current control circuit for the positive pulse may operate alternately to achieve bidirectional output of the electrical stimulation; two poles of the surface electrodes are connected across both ends of a bridge arm of the bridge constant-current source respectively to the equivalent resistance of the user R7.

In an embodiment, the functional electrical stimulation system further comprises n groups of electrical stimulation output channels. The central control unit is configured to generate the data packets of electrical stimulation parameters with time sequence information corresponding to the n groups of electrical stimulation output channels respectively, and send the data packets of electrical stimulation parameters to the corresponding electrical stimulation output channels respectively. In an embodiment, n=16.

In an embodiment, the functional electrical stimulation system further comprises an active discharge circuit. The central control unit is configured to generate an active discharge signal when the system is turned off, suspended or in an emergency stop state. One end of the active discharge circuit is connected to the energy storage module and the other end is connected to the ground, to receive an active discharge signal to release the electrical energy stored in the energy storage module.

In an embodiment, the active discharge circuit comprises: a third transistor Q3, an eighth resistor R8 and a ninth resistor R9; a collector of the third transistor Q3 is connected to the energy storage module via the eighth resistor R8, an emitter of the third transistor Q3 is connected to the ground, and a base of the third transistor Q3 is connected to the central control unit via the ninth resistor R9; wherein, when the system is in a normal mode, the third transistor Q3 is turned off and wherein, when the system is turned off, suspended or in the emergency stop state, the active discharge signal is set to a high level by the central control unit to turn on the third transistor Q3, and the electrical energy stored in the energy storage module is released via the eighth resistor R8.

In an embodiment, the functional electrical stimulation system further comprises an automatic discharge circuit having a control terminal connected to the primary power, the automatic discharge circuit is configured to release the electrical energy stored in the energy storage module when the output voltage of the primary power is lower than the first preset voltage.

In an embodiment, the automatic discharge circuit comprises a fourth transistor Q4, a fifth transistor Q5, a tenth resistor R10, an eleventh resistor R11, a twelfth resistor R12 and a thirteenth resistor R13; a base of the fourth transistor Q4 is connected to a primary power voltage signal via the thirteenth resistor R13, a collector of the fourth transistor Q4 is connected to the energy storage module via the tenth resistor R10, and an emitter of the fourth transistor Q4 is connected to the ground; a base of the fifth transistor Q5 is connected to the collector of the fourth transistor Q4 via the eleventh resistor R11, a collector of the fifth transistor Q5 is connected to the energy storage module via the twelfth resistor R12, and an emitter of the fifth transistor Q5 is connected to the ground; wherein, when the output voltage of the primary power is higher than the first preset voltage, the fourth transistor Q4 is turned on and the fifth transistor Q5 is turned off; and wherein, when the output voltage of the primary power is lower to the first preset voltage, the fourth transistor Q4 is turned off and the fifth transistor Q5 is turned on so as to release the electrical energy stored in the energy storage module via the twelfth resistor R12.

In an embodiment, the functional electrical stimulation system further comprises a fuse connected between the energy storage module and the electrical stimulation output channel, the fuse configured to disconnect a connection between the energy storage module and the electrical stimulation output channel when a level of the current outputted from the energy storage module is higher than a first preset current value. In an embodiment, the fuse is a 25 mA fast-blow fuse.

In an embodiment, the functional electrical stimulation system further comprises a voice-control emergency stop module configured to generate a voice-control emergency stop signal when a voice higher than a preset intensity or frequency is received and the central control unit is configured to generate the active discharge signal by the voice-control emergency stop signal; the active discharge circuit is configured to receive the active discharge signal to release the electrical energy stored in the energy storage module.

In an embodiment, the central control unit is configured to generate an alarm signal by the voice-control emergency stop signal and the functional electrical stimulation system further comprises an alarm circuit configured to receive the alarm signal to generate an audible and/or visual alarm signal.

In an embodiment, the functional electrical stimulation system further comprises a mechanical emergency stop module having a normally open contact connected between the energy storage module and the electrical stimulation output channel; wherein the normally open contact is turned on when the functional electrical stimulation system is in a normal mode, and the normally open contact is turned off when an emergency occurs so that a pathway between the energy storage module and the electrical stimulation output channel is disconnected. In an embodiment, the mechanical emergency stop module is a pressing-button switch, wherein the normally open contact is turned on when a user is treading or pressing the switch in the normal mode and the normally open contact is turned off when releasing the switch in an emergency.

In an embodiment, the functional electrical stimulation system further comprises a human-machine interaction module configured to receive the electrical stimulation parameters entered by the user; wherein the central control unit is connected to the human-machine interaction module, and configured to generate the data packets of electrical stimulation parameters based on the electrical stimulation parameters entered by the user, and transmit the data packets of electrical stimulation parameters to the electrical stimulation output channel.

In an embodiment, the functional electrical stimulation system further comprises a communication interface module configured to receive the data packets of electrical stimulation parameters inputted from a user terminal; wherein the central control unit is connected to the communication interface module, and configured to analyze the data packets of electrical stimulation parameters and package it into analyzable data packets of electrical stimulation parameters for the electrical stimulation output channel. In an embodiment, the electrical stimulation parameters included in the data packets of electrical stimulation parameters outputted from the user terminal contain electrical to stimulation waveform parameters obtained by modulating an audio signal, the user's real-time electromyographic signal and/or fixed waveform sequences. In an embodiment, the communication interface module comprises a RS232 communication interface.

Technical Effect

The functional electrical stimulation system may have one or more of the following advantages:
1) enhancing the flexibility and autonomy of electrical stimulation pulse, which can be beneficial for a user to select a personalized electrical stimulation pulse type according to his/her actual conditions.
2) providing multiple security protections and enhanced reliability to avoid danger in a normal mode.
3) the system operating as an independent device to produce electrical stimulation simply with fixed parameters, and/or operating as a computer peripheral controlled by a computer to produce the electrical stimulation with complicated time-varying parameters.

DETAILED DESCRIPTION

To make the purpose, technical scheme and advantages of present invention clear, a more detailed explanation for this invention is given by embodiments with reference to the drawings.

It should be noted that, in order to avoid confusing the information data signal connection (weak signal) with the functional electrical signal connection (strong signal), the embodiment just relates to the connection relationship of the functional electrical signal, and the connection relationship of the information data signal will only be described with the flow of the information data signal. In the present embodiment and each of the following embodiments, most of the components are not provided with the specific model and value except some special components that are different from the prior art. The applicant believes that those skilled in the art can select the specific model and value of the components after becoming aware of the above technical solutions. It should certainly fall into the scope of the present invention.

Figure 1:
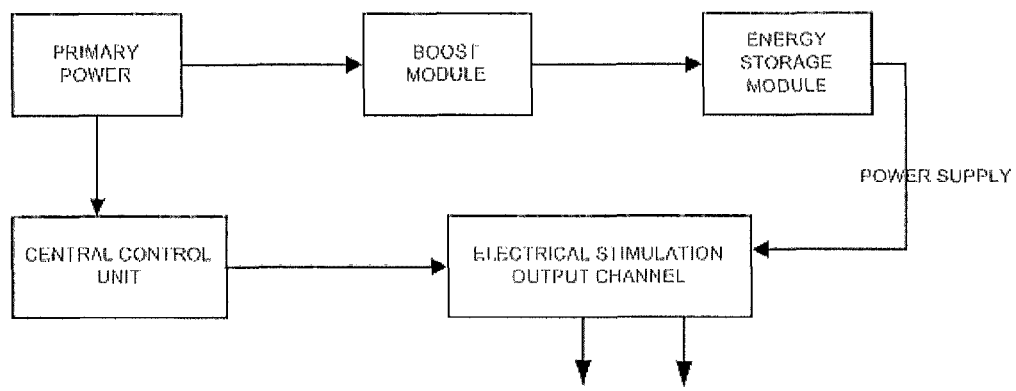
FIG. 1 is a structure diagram of a functional electrical stimulation system.

A functional electrical stimulation system according to an exemplary embodiment of the present invention is provided. FIG. 1 is a structure diagram of a functional electrical stimulation system. As shown in FIG. 1, the functional electrical stimulation system according to the exemplary embodiment of the present invention may include: a primary power; a boost module, connected to the primary power, configured to raise an output voltage of the primary power to a first preset voltage; an energy storage module, connected to the boost module, configured to store electrical energy of the first preset voltage; a central control unit configured to generate the data packets of electrical stimulation parameters; and an electrical stimulation output channel, connected to the energy storage module, configured to receive the data packets of electrical stimulation parameters, analyze the electrical stimulation parameters from the data packets, convert the electrical energy stored in the energy storage module to an electrical stimulation pulse according to the electrical stimulation parameters, and apply the electrical stimulation pulse to the diseased part of the user. In an embodiment, the primary power may be a 12V lithium battery, the boost module may be a DC boost module, and the energy storage module may be a capacitor with high-voltage (400V) resistance. The DC boost module raises the lithium battery voltage to 200V to power the electrical stimulation output channel.

According to an embodiment, the electrical stimulation output channel outputs the electrical stimulation pulse in accordance with the data packets of electrical stimulation parameters from the central control unit so as to enhance the flexibility and autonomy of selecting the electrical stimulation pulse, which can be beneficial for a user to select a personalized electrical stimulation pulse type according to his/her actual conditions.

Figure 2:
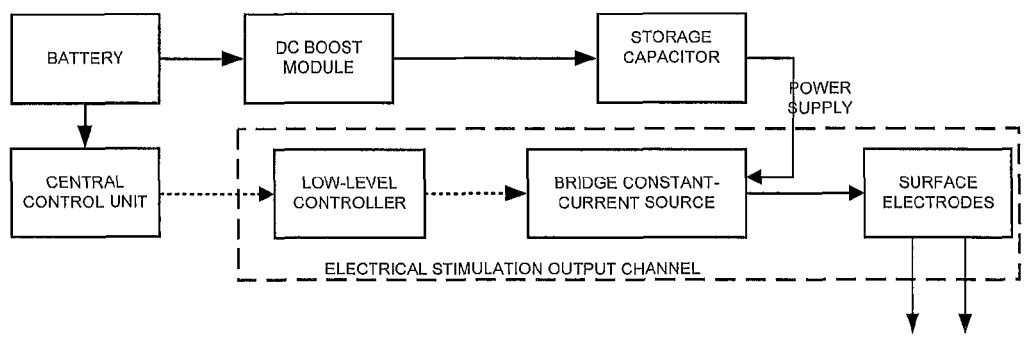
FIG. 2 is a structure diagram of the functional electrical stimulation system according to an embodiment of present invention.

As shown in FIG. 2, in order to achieve a stable and reliable output of electrical stimulation pulse, according to an embodiment of the invention, the electrical stimulation output channel may include: a low-level controller configured to receive the data packets of electrical stimulation parameters from the central control unit, analyze the electrical stimulation parameters from the data packets, and output a positive control signal and a negative control signal according to the electrical stimulation parameters respectively; a constant-current source, connected to the energy storage module, configured to receive the positive control signal and the negative control signal, convert the electrical energy stored in the energy storage module to a bipolar electrical stimulation pulse according to the positive control signal and the negative control signal; surface electrodes having two poles connected to two output ends of the constant-current source respectively, and configured to apply the bipolar electrical stimulation pulse to the diseased part of the user. In an embodiment, the constant-current source is a bridge constant-current source, and two poles of the surface electrodes are connected across both ends of a bridge arm of the bridge constant-current source respectively.

Figure 6:
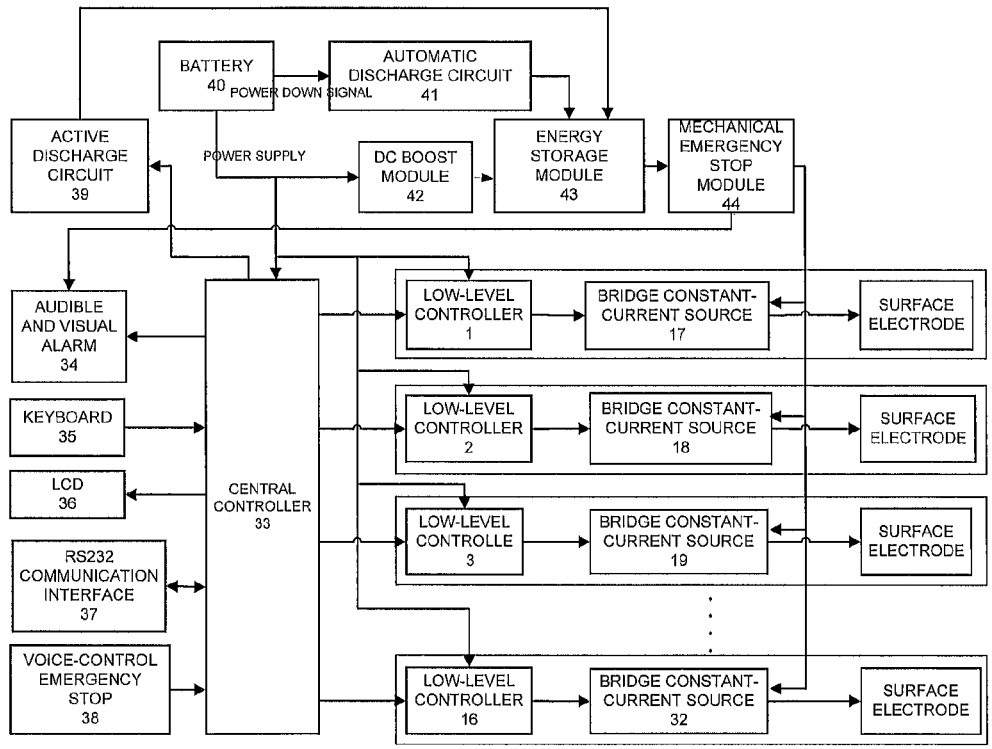
FIG. 6 is a structure diagram of the functional electrical stimulation system according to an embodiment of present invention.

In order to achieve multi-channel output of the electrical stimulation pulse, according to an embodiment of the invention, the functional electrical stimulation system may include n groups of electrical stimulation output channels. The central control unit is configured to generate the data packets of electrical stimulation parameters with time sequence information corresponding to the n groups of electrical stimulation output channels respectively, and then send the data packets of electrical stimulation parameters to the corresponding electrical stimulation output channels respectively. In an embodiment, as shown in FIG. 6, the functional electrical stimulation system may include 16 groups of electrical stimulation output channels. The control signal for the low-level controller and the bridge constant-current source can control a current polarity through a switch quantity and control current amplitude through an analog quantity.

Figure 3:
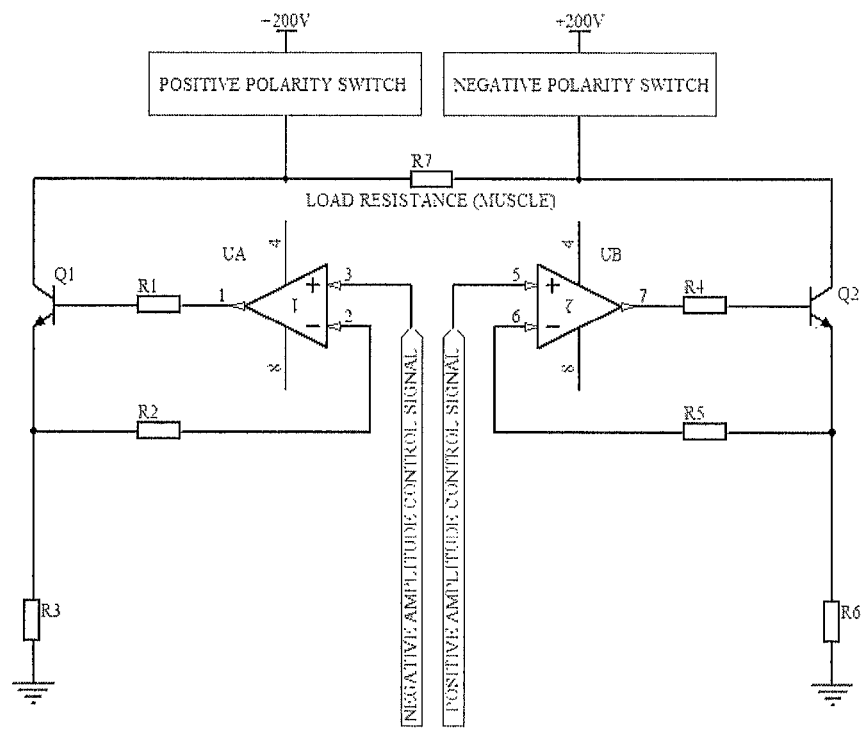
FIG. 3 is a schematic diagram of an electrical stimulation output channel in the functional electrical stimulation system according to an embodiment of present invention.

FIG. 3 is a schematic diagram of an electrical stimulation output channel in the functional electrical stimulation system according to an embodiment of present invention. As shown in FIG. 3, the bridge constant-current source may include: an operational amplifier UA, an operational amplifier UB, a resistor R1, a resistor R2, a resistor R3, a resistor R4, a resistor R5, a resistor R6, a transistor Q1 and a transistor Q2; the operational amplifier UA, the resistor R1, the resistor R2 and the resistor R3 form a constant-current control circuit for a negative pulse; a positive input end of the operational amplifier UA is connected to the negative control signal generated by the low-level controller to control the amplitude of a negative pulse current; the resistor R1 is connected to a output end of the operational amplifier UA and a base of the transistor Q1; the resistor R2 is connected to a negative input end of the operational amplifier UA and an emitter of the transistor Q1; the resistor R3 is connected to the emitter of the transistor Q1 and the ground; a collector of the transistor Q1 is connected to the output of the boost module via a positive polarity switch. The operational amplifier UB, the resistor R4, the resistor R5, the resistor R6 and the resistor R7 form a constant-current control circuit for a positive pulse; a positive input end of the operational amplifier UB is connected to the positive control signal generated by the low-level controller to control the amplitude of a positive pulse current; the resistor R4 is connected to a output end of the operational amplifier UB and a base of the transistor Q2; the resistor R5 is connected to a negative input end of the operational amplifier UB and an emitter of the transistor Q2; the resistor R6 is connected to the emitter of the transistor Q2 and the ground; a collector of the transistor Q2 is connected to the output of the boost module via a negative polarity switch. The constant-current control circuit for the negative pulse and the constant-current control circuit for the positive pulse may operate alternately to achieve the bidirectional output of the electrical stimulation.

It should be noted that the transistor in the bridge constant-current source circuit described above may be replaced by a field effect transistor; the whole constant-current source may be achieved through the discrete components mentioned above and also may be achieved through an integrated chip having a function of constant-current source, which fall into the scope of an embodiment of the present invention.

Residual electrical energy may be stored in the energy storage unit when the system is turned off, suspended or in the emergency stop state. In this case, it is likely that there is a danger caused by the energy. According to an embodiment of the invention, the functional electrical stimulation system may additionally include an active discharge circuit. The central control unit is configured to generate an active discharge signal when the system is turned off, suspended or in the emergency stop state. One end of the active discharge circuit is connected to the energy storage module and the other end is connected to the ground. The active discharge circuit is configured to receive the active discharge signal to release the electrical energy stored in the energy storage module.

Figure 4:
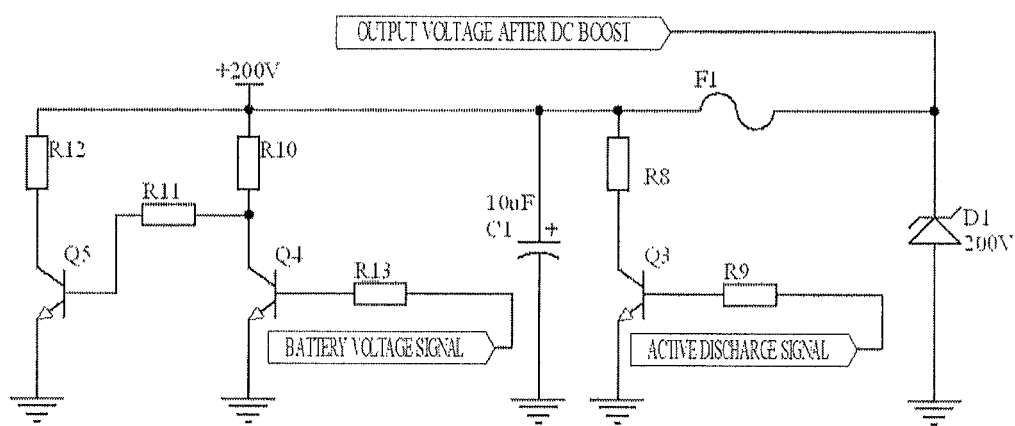
FIG. 4 is a schematic circuit diagram for DC boosting, automatic discharging and over-current protection in the functional electrical stimulation system according to an embodiment of present invention.

FIG. 4 is a schematic circuit diagram of DC boost, automatic discharge and over-current protection in the functional electrical stimulation system according to an embodiment of present invention. As shown in FIG. 4, the active discharge circuit may include: a transistor Q3, a resistor R8 and a resistor R9; a collector of the transistor Q3 is connected to the energy storage module via the resistor R8, an emitter of transistor Q3 is connected to the ground, and a base of transistor Q3 is connected to the central control unit via the resistor R9; when the system operates in the normal mode, the transistor Q3 is turned off; when the system is turned off, suspended or in the emergency stop state, the active discharge signal is set to the high level by the central control unit to turn on the transistor Q3, and the electrical energy stored in the energy storage module is released via the resistor R8. In addition, the transistor described above may be replaced by any other switching element.

When the system is switched down abruptly due to low battery or a disconnected battery, the central controller as well as the back-end output circuit cannot operate because there is no power supply. The energy will be stored in the capacitor, which is likely to cause safety problems.

In an embodiment, the functional electrical stimulation system may additionally include an automatic discharge circuit having a control terminal, connected to the battery, configured to release the electrical energy stored in the energy storage module when the battery voltage is lower than a first preset voltage (for example, 0.7V). The automatic discharge circuit is turned off when the system operates in the normal mode. An example of the situation in which the battery voltage is lower than the preset voltage is that the battery powers down abruptly.

As shown in FIG. 4, the automatic discharge circuit may include a transistor Q4, a transistor Q5, a resistor R10, a resistor R11, a resistor R12 and a resistor R13; a base of the transistor Q4 is connected to a battery signal via the resistor R13, a collector of the transistor Q4 is connected to the energy storage module via the resistor R10, and an emitter of the transistor Q4 is connected to the ground; a base of the transistor Q5 is connected to the collector of the transistor Q4 via the resistor R11, a collector of the transistor Q5 is connected to the energy storage module via the resistor R12, and an emitter of the transistor Q5 is connected to the ground; when the output voltage of the primary power is higher than the first preset voltage (a typical example of the battery in a normal mode), the transistor Q4 is turned on and the transistor Q5 is turned off; and when the output voltage of the primary power is lower than the first preset voltage (a typical example is the battery powers down abruptly), the transistor Q4 is turned off and the transistor Q5 is turned on so as to release the electrical energy stored in the energy storage module via the resistor R12.

Meanwhile, in order to further ensure the user's safety, the functional electrical stimulation system may additionally include a fuse connected between the energy storage module and the electrical stimulation output channel. The fuse is configured to disconnect the connection between the energy storage module and the electrical stimulation output channel when the level of the current outputted from the energy storage module is higher than the first preset current value. In an embodiment, the fuse is a 25 mA fast-blow fuse.

In order to further ensure the user's safety, according to an embodiment of the invention, the functional electrical stimulation system may additionally include an emergency stop protection device. The emergency stop protection device is used to handle an emergency, such as an abnormal heartbeat or a muscle spasm caused by electrical stimulation. When the user cannot turn off the system or remove the electrodes, the emergency stop protection device may cut off the output channel and power source quickly, and send an audible and visual alarm signal in time so as to ensure the user's safety. The emergency stop protection device may include a voice-control emergency stop module, a mechanical emergency stop module and/or an alarm module. Each module will be described in detail hereinafter.

Figure 5:
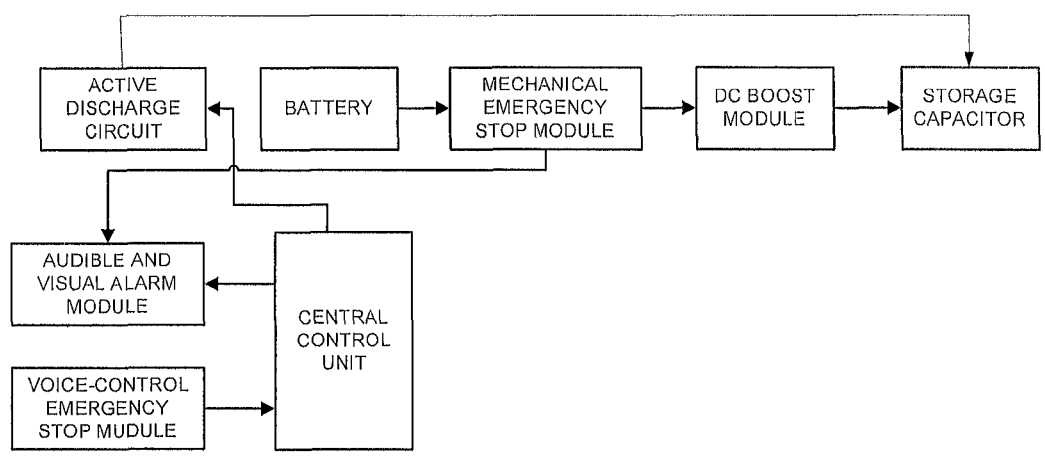
FIG. 5 is a structure diagram of the functional electrical stimulation system according to an embodiment of present invention.

FIG. 5 is a structure diagram of the functional electrical stimulation system according to an embodiment of present invention. As shown in FIG. 5, the functional electrical stimulation system may further include the voice-control emergency stop module configured to generate a voice-control emergency stop signal when a voice higher than a preset intensity or frequency is received. The central control unit is configured to generate the active discharge signal by the voice-control emergency stop signal. The active discharge circuit is configured to receive the active discharge signal to release the electrical energy stored in the energy storage module.

As shown in FIG. 5, the functional electrical stimulation system may additionally include a mechanical emergency stop module having a normally open contact connected between the energy storage module and the electrical stimulation output channel. The normally open contact is turned on when the functional electrical stimulation system is in a normal mode, while the normally open contact is turned off when an emergency occurs so that a pathway between the primary power and the electrical stimulation output channel is disconnected. In an embodiment, the mechanical emergency stop module is a pressing-button switch; the normally open contact is turned on when a user is treading or pressing the switch in the normal mode; the normally open contact is turned off when the user releases the switch in emergency.

Whether it is the voice-control emergency stop or the mechanical emergency stop, any kind of switch can cut off the output of electrical stimulation and give an audible and visual alarm meanwhile when an emergency occurs.

To make it convenient for the user to set the electrical stimulation parameters, according to an embodiment of the invention, the functional electrical stimulation system may operate in two operation modes, that is "Stand-alone" and "PC-monitor".

When operating in "Stand-alone" mode, the functional electrical stimulation system may include a human-machine interaction module configured to receive the electrical stimulation parameters entered by a user. In this mode, the central control unit is connected to the human-machine interaction module and configured to generate the data packets of electrical stimulation parameters based on the electrical stimulation parameters entered by the user, and transmit the data packets of electrical stimulation parameters to the electrical stimulation output channel.

When operating in "PC-monitor" mode, the functional electrical stimulation system may include the communication interface module configured to receive the data packets of electrical stimulation parameters inputted from a user terminal. The central control unit is connected to the communication interface module and configured to analyze the data packets of electrical stimulation parameters and package it into the analyzable data packets of electrical stimulation parameters for the electrical stimulation output channel. In an embodiment, the electrical stimulation parameters included in the data packets of electrical stimulation parameters may contain the electrical stimulation waveform parameters obtained by modulating the audio signal, the user's real-time electromyographic signal and the fixed waveform sequences. In an embodiment, the communication interface module is a RS232 communication interface.

A desirable embodiment of the present invention will be described on the basis of the above embodiment. It should be noted that this desirable embodiment is only for understanding of the present invention, and is not intended to limit the scope of the present invention. Further, features of the desirable embodiment are all applicable to the embodiment of the respective devices unless context dictates otherwise. It will be readily understood that the aspects of the present disclosure, as generally described herein, and illustrated in the Figures, can be arranged, substituted, combined, and designed in a wide variety of different configurations, all of which are explicitly contemplated and are made part of this disclosure.

FIG. 6 is a structure diagram of the functional electrical stimulation system according to an embodiment of present invention. The functional electrical stimulation system may include a central control unit 33, a battery 40, a DC boost module 42, a storage capacitor 44, an active discharge circuit 39, an automatic discharge circuit 41, bridge constant-current sources 17-32, low-level controllers 1-16, an emergency stop protection module, a human-machine interaction module and a RS232 communication interface 37. The bridge constant-current sources are arranged corresponding to the low-level controllers respectively so as to form a 16 channel output module of electrical stimulation. This output module enables the electrical stimulation to act on human body via a pair of surface electrodes. The emergency stop protection module may include the mechanical emergency stop module 44, the voice-control emergency stop module 38 and the audible and visual alarm module 34. The human-machine interaction module may include a keyboard 35 and a LCD 36. The whole system is powered by a 12V lithium battery and the DC boost module raises the battery voltage to 200V to power the constant-current output circuit. The voltage-controlled constant-current source is used in the constant-current output circuit, which outputs a current with a range of 0-100 mA. The bridge circuit may be composed of two groups of transistors and change the polarity of current by switching the status of transistors with control signals provided by the corresponding low-level controller. One low-level controller and a bridge constant-current output circuit form one electrical stimulation output channel. The low-level controller is controlled by the central control unit through an I2C bus. The system contains 16 electrical stimulation output channels, which can act on a plurality of muscles at the same time so as to assist the user to complete a certain action by stimulating these muscles with the corresponding time sequence.

The central control unit 33 shown in FIG. 6 is a C8051F340 microcontroller, which is a principal chip of the entire system. The central control unit is configured to: drive the LCD 36; read information transmitted via the keyboard 35; communicate with the low-level controllers 1-16 through the integrated I2C bus; activate the active discharge circuit 39 to avoid the energy accumulation when the system is turned off or in the suspended state; respond to an urgent interrupt signal generated by the voice-control emergency stop module 38; drive the audible and visual alarm module 34; activate the active discharge circuit 39 while cutting off the electrical stimulation; when operating in "PC-monitor" mode, receive the control signals transmitted from a computer via the RS232 communication interface 37; and distribute analysis results to the low-level controllers 1-16 of the corresponding channels after analyzing the signals.

Each electrical stimulation output channel shown in FIG. 6 may include one of the low-level controllers 1-16 and a corresponding bridge constant-current source from 17-32. The low-level controller may be C8051F410 microcontroller, which integrates dual DA function to control the constant-current source. The schematic circuit diagram of the bridge constant-current source is shown in FIG. 3. The bridge structure is used in the constant-current source to achieve the bipolar output of electrical stimulation. A load resistance stimulating the muscle of human body, is connected in series to the bridge arm of H-bridge via the surface electrodes. The direction of the current flowing through the load resistance can be switched by controlling the polarity switch and the state of transistor. When the positive polarity switch and transistor Q2 turn on as well as the negative polarity switch and transistor Q1 turn off, the direction of the current flowing from the left of the load resistance R7 to the right is defined as the positive direction. On the other hand, when the positive polarity switch and transistor Q2 turns off as well as the negative polarity switch and transistor Q1 turns on, the direction of the current flowing from the right of the load resistance R7 to the left is defined as the negative direction. The transistor Q1 and the operational amplifier UA as well as the transistor Q2 and the operational amplifier UB form two sets of constant-current sources respectively. The operational amplifiers UA and UB are implemented by LM358 chips.

The principle of constant-current source will now be described with reference to the constant-current source composed of amplifier UB and transistor Q2. A positive amplitude control signal generated by the low-level controller C8051F410 is an analog signal of 0-3V. When the positive amplitude control signal is inputted to an in-phase input of the operational amplifier UB, a voltage to ground of a sampling resistance R6 is approximately equal to the amplitude of the positive amplitude control signal according to a virtual short circuit theory. When the sampling resistance R6 is 30Ω, the range of current flowing through resistor R6 is 0-100 mA. As the current flowing through resistor R6 is rarely from resistor R4 or resistor R5, it can be considered that the current flowing through resistor R7 is approximately equal to the current flowing through resistor R6, that is, 0-100 mA. A load resistance R7 is the muscle of human body to be stimulated, which can change its value according to the external environment. The load resistance R7 may be reduced to about 1KΩ-2KΩ after wiping skin with alcohol. In the case of a maximum of 2KΩ, the voltage to provide 100 mA constant-current stimulation is 200V. Therefore, the DC boost module may need to raise the battery voltage to at least 200V.

Figure 7:
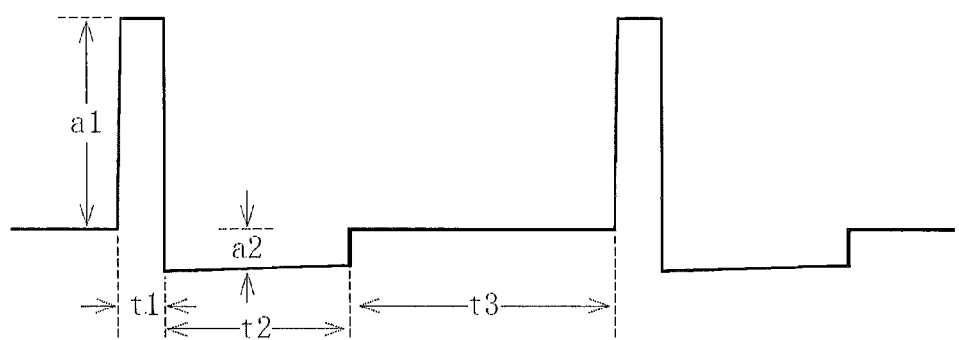
FIG. 7 is a waveform diagram outputted from one electrical stimulation channel in the functional electrical stimulation system according to an embodiment of present invention.

FIG. 7 is a waveform diagram outputted from one electrical stimulation channel in the functional electrical stimulation system according to an embodiment of present invention. In a first stage, the microcontroller C8051F410 turns on the positive polarity switch to output a positive amplitude control signal with a positive pulse amplitude a1, while C8051F410 turns off the negative polarity switch to set a negative amplitude control signal to zero. Accordingly, the current can flow through the load resistance in the positive direction with the necessary amplitude. This stage may last for t1, so as to output the positive pulse with a pulse width of t1. In a second stage, microcontroller C8051F410 turns on the negative polarity switch to output the negative amplitude control signal with a negative pulse amplitude a2, while microcontroller C8051F410 turns off the positive polarity switch to set the positive amplitude control signal to zero. Accordingly, the current can flow through the load resistance in the negative direction with the necessary amplitude. This stage may last for t2, so as to output the negative pulse with a pulse width of t2. In a third stage, the positive and negative polarity switches are both turned off, so that both of the positive and negative amplitude control signals are zero as well. There is no current flowing through the load resistance. This stage may last for t3, which is an interval between two electrical stimulation pulses. A pulse cycle T is a sum of the duration of the three stages, and a pulse frequency is an inverse of the pulse cycle T. Setup parameters of the electrical stimulation output channel may be set in a range of: a positive pulse width of 0-1000 μs, a negative pulse width of 0-3000 μs, a positive pulse amplitude of 0-100 mA, a negative pulse amplitude of 0-50 mA and a pulse frequency of 0-100 Hz.

Since the high voltage of 200V for the bridge constant-current output circuit is stored in an electrolytic capacitor with a large capacity, the energy in the capacitor will be released via the discharge circuit automatically when the system is turned off, powers down abruptly or is in a resting phase between two sections of electrical stimulation, so as to avoid an accident due to long time storage.

FIG. 4 is a schematic circuit diagram for DC boosting, automatic discharging and over-current protection in the functional electrical stimulation system according to an embodiment of present invention. The battery voltage is increased by the DC boosting to 200V by an inductor. A 10μF electrolytic capacitor C1 of 400V high-voltage resistance is connected in parallel at a back end of the battery, so as to keep the voltage stable when outputting electrical stimulation pulse. The transistor Q3 in the active discharge circuit is controlled by the active discharge signal provided by the master chip. The active discharge signal is usually in a low level state so that the transistor Q3 is turned off. When the active discharge is needed, such as the system is turned off, suspended or in an emergency stop mode, the active discharge signal is set to the high level by the central control unit to turn on transistor Q3 so that the high-voltage energy stored in the capacitor C1 is released through the ground loop established by resistor R8.

When the system is powered down abruptly due to low battery voltage or a loose battery, the central control unit and the output circuit cannot operate normally without power supply. The energy will be stored in the capacitor, which is likely to cause safety problems. Therefore the automatic discharge circuit guarantees the user's safety. The battery voltage of 12V turns on transistor Q4 in a normal operating mode. The voltage at the collector of transistor Q4 having a turn-on voltage of 0.2V is not enough to turn on transistor Q5. Resistor R10 is a high-impedance resistance with only 0.1 μA current flowing through. Therefore, the discharge will not occur. When the battery voltage signal disappears without the power supply, transistor Q4 is turned off and the voltage at the collector of transistor Q4 is pulled up to 200V by resistor R10, which is sufficient to turn on transistor Q5 so that the stored energy is released through a ground loop established by resistor R12.

F1 shown in FIG. 4 is a 25 mA fast-blow fuse. Although a peak value of pulse current may be 100 mA, the fuse does not blow out in the normal operation mode because a duty ratio of pulse current is small and an average current (below 1-2 mA) is less than a body safety current. When an excessive current flows through the human body constantly due to a system failure, the fuse may be blown out rapidly to protect the user's security. As known in the art, when the average current flowing through the human body is greater than 90-100 mA, the human will likely have a symptom of respiratory paralysis, when the excessive current lasts around 3 min or longer, have a heart attack or have the heart stop beating, and when the average current flowing through the human body is 20-25 mA, the human will feel pain in fingers, increased burning sensation and spasm in the hand muscles and the like. This will not cause a life-threatening condition immediately. Therefore, a fuse with 25 mA fusing current is selected to achieve an adequate safety allowance.

The emergency stop protection device is used to handle the emergency, such as the abnormal heartbeat or muscle spasm caused by electrical stimulation. When the user cannot turn off the system or remove the electrodes, the emergency stop protection device may cut off the output channel, turn off the power source in time, and send an audible and/or visual alarm signal so as to ensure the user's safety. The emergency stop protection module shown in FIG. 6 may include a voice-control emergency stop module 38, a mechanical emergency stop module 44 and an alarm module 34. The voice-control emergency stop module is a voice-control switch, which can generate a jumping signal when the system receives a sound with a certain intensity. The signal is connected to an interrupt pin of the central control unit 33 to trigger an emergency stop interrupt. A user or medical staff may not be able to turn off the equipment immediately when an emergency occurs, which may cause continuous harm to the user. So, an advantage of the voice-control switch is fast response. The voice-control switch can be activated in response to a shout from the user or medical staff, so that the electrical stimulation is stopped promptly. The voice-control emergency stop switch operates depending on a normal operation of the central controller. However, when the system is influenced by an unexpected change such as electromagnetic interference so that the central control unit may have something wrong or an error, the voice-control switch cannot operate in a normal mode and the mechanical emergency stop switch 42 has to be used. The mechanical emergency stop module is a pressing-button switch having a normally open contact connected between the energy storage module and the electrical stimulation output channel while a normally closed contact connected to the audible and visual alarm. When a user is treading or pressing the switch in the normal mode, the normally open contact is turned on to connect the path between the battery and the DC boost module while the normally closed contact is turned off and the audible and/or visual alarm does not operate. When the user is releasing the switch in an emergency, the normally open contact is turned off so that a pathway between the battery and the DC boost module is disconnected to stop the output of electrical stimulation, while the normally closed contact is turned on so that the audible and visual alarm module will receive a START signal to send out an alert signal.

The system can be operated in the two modes, the "Stand-alone" mode and the "PC-monitor" mode, for different operation environments. The same preparation operation may be used for these two operation modes: the surface electrodes of each channel are attached to the muscle to be stimulated; the hand-held mechanical emergency stop switch is used for the electrical stimulation of a lower limb and the tread-type mechanical emergency stop switch is used for the electrical stimulation of upper limb. Next, upon switching on the power supply, the various peripherals of the system are initialized and a prompt message is displayed on an LCD for selecting the operation mode. If a user selects the "Stand-alone" mode, the user is prompted to input the electrical stimulation parameters of each channel. The user could set the parameters, such as frequency, positive/negative pulse width and positive/negative pulse amplitude, based on previous experience. Corresponding data packets are generated based on the setup parameters generate by the central control unit, and then transmitted to the low-level controller of the relevant channel through the data bus. The low-level controller analyzes the data packets and outputs the electrical stimulation with the corresponding time sequence. If the user feels discomfort and needs a break, the electrical stimulation can be suspended by using the keyboard. The electrical stimulation may be continued after a period of time. When an unexpected circumstance occurs, for example, a muscle spasm, the electrical stimulation can't be turned off by using the keyboard immediately. Thus the voice-control emergency stop circuit is activated by a shout from the user and the stored energy is released automatically to stop electrical stimulation. Alternatively, the mechanical emergency stop switch may be used by the user to cut off the power supply directly. The mechanical emergency stop switch and/or the voice-control emergency stop switch activate the audible and visual alarm circuit to output an alarm. Because a computing speed and a memory space of the microcontroller are limited, the microcontroller used as the central control unit may restrict the application of the system. Therefore, the "PC-monitor" mode is used to generate the real-time electrical stimulation parameters by using the computer and the real-time electrical stimulation parameters are transmitted to the low-level controller of each channel via the central control unit to achieve complex control. The process of the "PC-monitor" mode may described as follows. A preparation operation in the "PC-monitor" mode is same as that of the "Stand-alone" mode. The user may select the "PC-monitor" mode when the prompt message is displayed on the LCD. Then the central control unit waits until it receives data packets from the computer. After receiving a data packet, the central control unit analyzes the packet and packages it into an analyzable format to be transmitted to the low-level controller. A total time for the process of transmission and analyzing is less than 100 μs, thus a real-time control with respect to the responding of human muscles can be achieved. Generally, there are two ways for generating a final output of desired waveform in the "PC-monitor" mode. A first way involves generating the output by modulating the pulse signal with a random music. An advantage of randomness can be achieved so as to avoid a decreased sensitivity to the electrical stimulation and therapeutic effect due to a long-term use of fixed stimulation parameters. A second way involves generating the output by modulating the pulse signal with the electromyographic signal obtained by an EMG acquisition instrument connected to a computer. An advantage is that the intensity of electrical stimulation can be controlled through the independent movement by the user. For example, a hemiplegic patient can control the stimulation intensity on a paralyzed body side via the limb of a healthy side.

Figure 8:
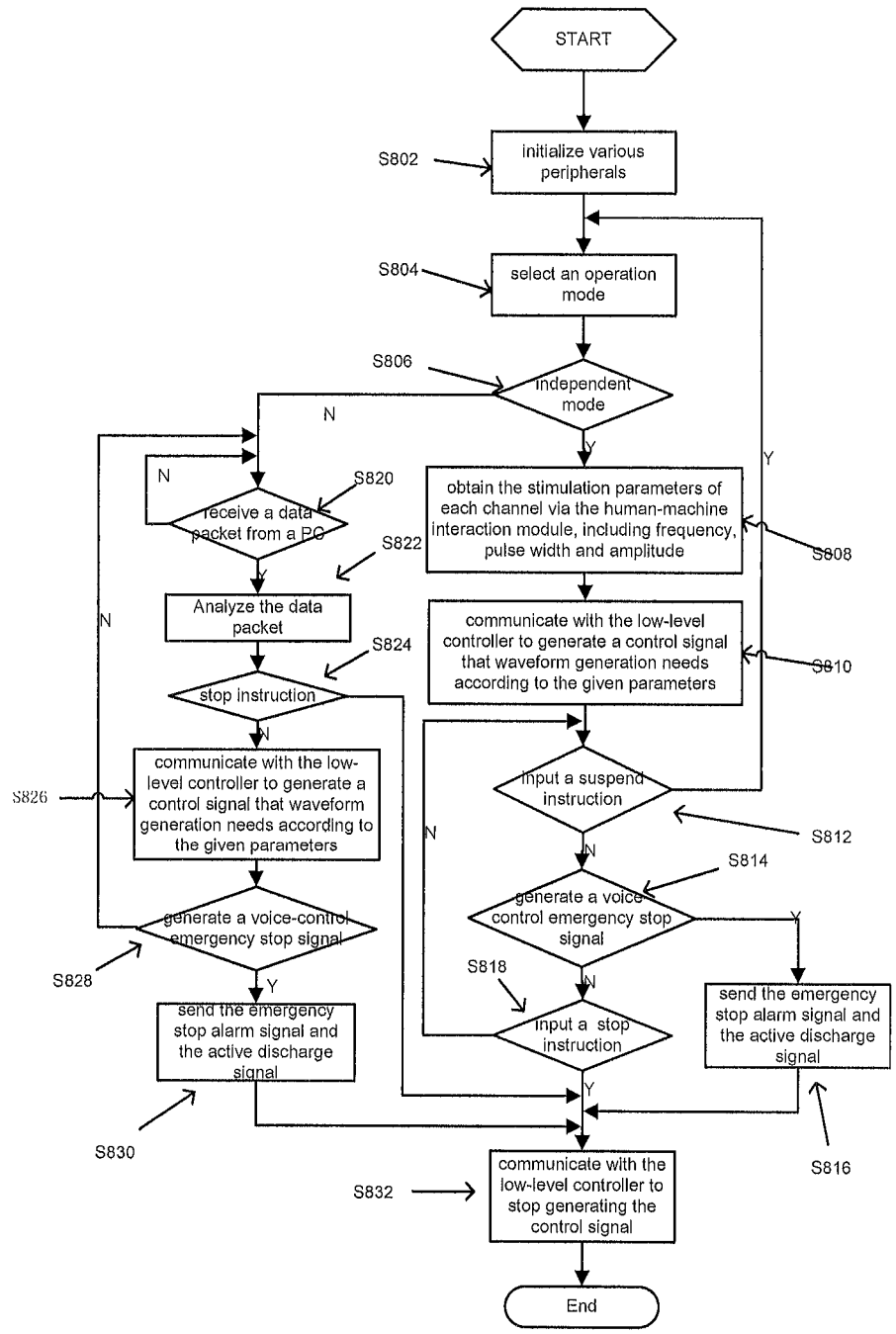
FIG. 8 is a control flow diagram of a central controller in the functional electrical stimulation system according to an embodiment of present invention.

FIG. 8 is a control flow diagram of a central controller in the functional electrical stimulation system according to an embodiment of present invention. As shown in FIG. 8, the control flow of the central controller may include:

Step S802: initializing various peripherals;

Step S804: selecting an operation mode, that is selecting an independent mode or a user terminal controlled mode;

Step S806: determining whether the operation mode selected by the user is the independent mode or not. If yes, performing a Step S808; if no, performing Step S820;

Step S808: obtaining the stimulation parameters of each channel via the human-machine interaction module; and the central controller sends a control signal to the low-level controller to output the electrical stimulation;

Step S810: transmitting the stimulation parameters to the low-level controller;

Step S812: determining whether a suspend instruction is inputted from the keyboard. If yes, performing Step S804; if no, performing Step S814;

Step S814: determining whether the voice-control emergency stop signal is generated. If yes, performing Step S816; if no, performing Step S818;

Step S816: sending the emergency stop alarm signal and the active discharge signal, and then performing Step S832;

Step S818: determining whether a stop running instruction is inputted from the keyboard. If yes, performing Step S832; if no, performing Step S812;

Step S820: determining whether a data packet entered from the user terminal is received. If yes, performing Step S822; if no, repeating Step S820;

Step S822: analyzing the data packet;

Step S824: determining whether a stop instruction is received from a host computer. If yes, performing Step S832; if no, performing Step S826;

Step S826: transmitting the stimulation parameters to the low-level controller;

Step S828: determining whether the voice-control emergency stop signal is generated. If yes, performing Step S830; if no, performing Step S820;

Step S830: sending the emergency stop alarm signal and the active discharge signal, and then performing Step S832;

Step S832: transmitting the stop instruction to the low-level controller and ending the flow.

Figure 9:
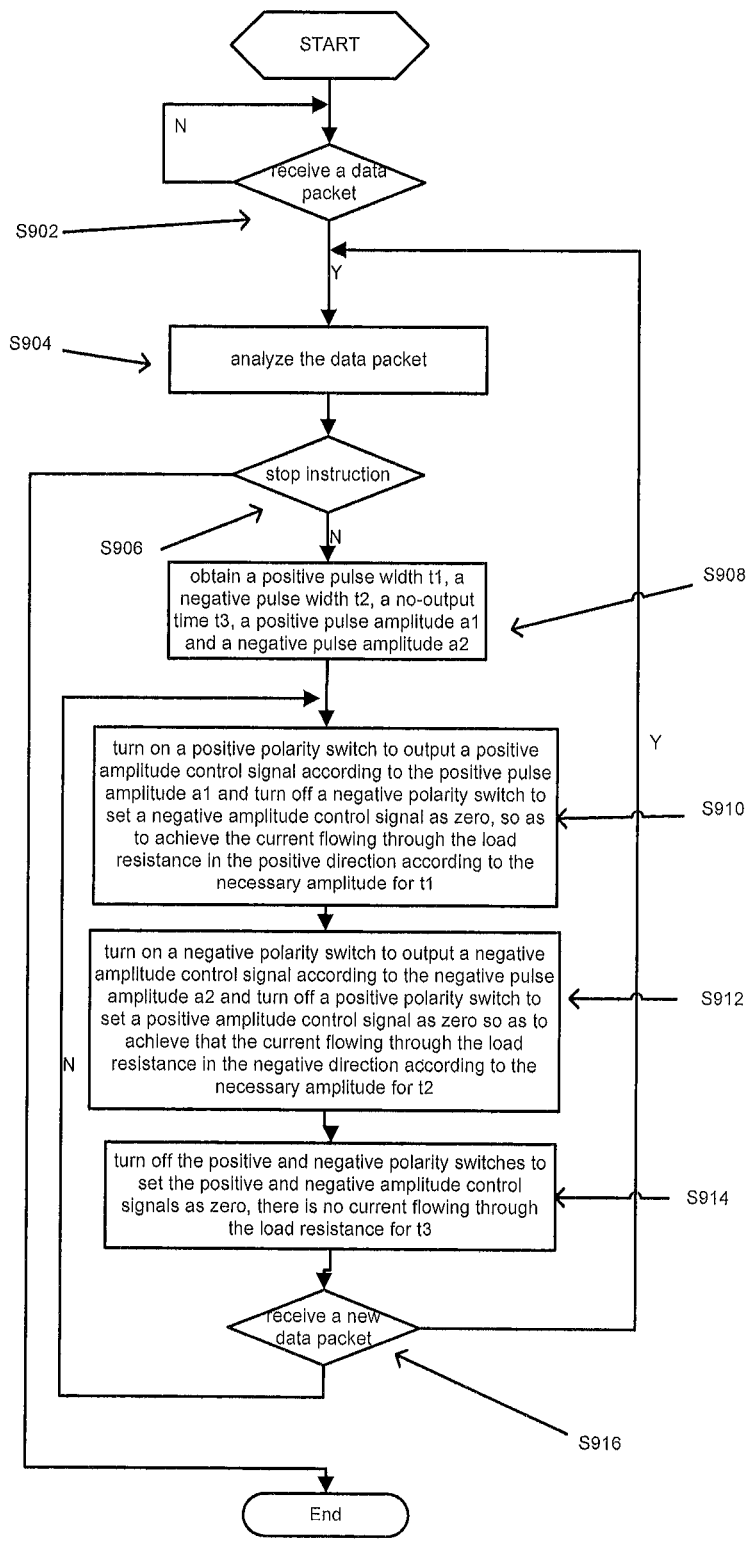
FIG. 9 is a control flow diagram of a low-level controller in the functional electrical stimulation system according to an embodiment of present invention.

FIG. 9 is a control flow diagram of a low-level controller in the functional electrical stimulation system according to an embodiment of present invention. As shown in FIG. 9, the control flow of the low-level controller may include:

Step S902: determining whether a data packet is received from the user terminal. If yes, performing Step S904; if no, repeating Step S902;

Step S904: analyzing the data packet;

Step S906: determining whether a stop instruction is received. If yes, the process is finished; if no, performing Step S908;

Step S908: obtaining the parameters of electrical stimulation pulse for one cycle;

Step S910: outputting a positive pulse in accordance with the obtained positive pulse parameters;

Step S912: outputting a negative pulse in accordance with the obtained negative pulse parameters;

Step S914: stopping output;

Step S916: determining whether a new data packet is received. If yes, performing Step S904; if no, performing Step S910;

In general, compared with the prior art, the present embodiment increases the number of electrical stimulation output channels, and enhances the security measures so as to alleviate the user's fear during the normal use. In addition, a secondary damage caused by the FES, such as abnormal heart beat and muscle spasm, can be avoided effectively. Two operation modes make the present embodiment able to achieve electrical stimulation simply with fixed parameters, and also achieve electrical stimulation with complicated time-varying parameters.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A functional electrical stimulation system comprising:
a boost module, connected or connectable to a primary power, configured to raise an output voltage of the primary power to a first preset voltage;
an energy storage module, connected to the boost module, configured to store electrical energy of the first preset voltage;
a central control unit configured to generate the data packets of electrical stimulation parameters; and
an electrical stimulation output channel, connected to the energy storage module, and configured to receive the data packets of electrical stimulation parameters, analyze the electrical stimulation parameters from the data packets, convert electrical energy stored in the energy storage module to an electrical stimulation pulse corresponding to the electrical stimulation parameters, and apply the electrical stimulation pulse to a diseased part of a user.

2. The functional electrical stimulation system according to claim 1, wherein the electrical stimulation output channel comprises:
a low-level controller configured to receive the data packets of electrical stimulation parameters from the central control unit, analyze the electrical stimulation parameters from the data packets, and output a positive control signal and a negative control signal corresponding to the electrical stimulation parameters respectively;
a constant-current source, connected to the energy storage module, configured to receive the positive control signal and the negative control signal, and convert electrical energy stored in the energy storage module to a bipolar electrical stimulation pulse according to the positive control signal and the negative control signal; and
a surface electrode having two poles connected to two output ends of the constant-current source respectively, the surface electrode configured to apply the bipolar electrical stimulation pulse to the diseased part of the user.

3. The functional electrical stimulation system according to claim 2, wherein the constant-current source is a bridge constant-current source comprising a first operational amplifier, a second operational amplifier, a first resistor, a second resistor, a third resistor, a fourth resistor, a fifth resistor, a sixth resistor, a first transistor, and a second transistor;
wherein the first operational amplifier, the first resistor, the second resistor, the third resistor and an equivalent resistance of the user form a constant-current control circuit for a negative pulse; a positive input end of the first operational amplifier is connected to the negative control signal generated by the low-level controller to control an amplitude of a negative pulse current; the first resistor is connected to an output end of the first operational amplifier and a base of the first transistor; the second resistor is connected to a negative input end of the first operational amplifier and an emitter of the first transistor; the third resistor is connected to the emitter of the first transistor and a ground; a collector of the first transistor is connected to the output of the boost module via a positive polarity switch;
wherein the second operational amplifier the fourth resistor, the fifth resistor, the sixth resistor and the equivalent resistance of the user form a constant-current control circuit for a positive pulse; a positive input end of the second operational amplifier is connected to the positive control signal generated by the low-level controller to control an amplitude of a positive pulse current; the fourth resistor is connected to an output end of the second operational amplifier and a base of the second transistor; the fifth resistor is connected to a negative input end of the second operational amplifier and an emitter of the second transistor; the sixth resistor is connected to the emitter of the second transistor and the ground; a collector of the second transistor is connected to the output of the boost module via a negative polarity switch;

wherein the constant-current control circuit for the negative pulse and the constant-current control circuit for the positive pulse are configured to operate alternately to achieve bidirectional output of the electrical stimulation; and wherein two poles of the surface electrode are connected across both ends of a bridge arm of the bridge constant-current source respectively to the equivalent resistance of the user.

4. The functional electrical stimulation system according to claim 2, further comprising n groups of electrical stimulation output channels;

wherein the central control unit is configured to generate the data packets of electrical stimulation parameters with time sequence information corresponding to the n groups of electrical stimulation output channels respectively, and send the data packets of electrical stimulation parameters to the corresponding electrical stimulation output channels respectively.

5. The functional electrical stimulation system according to claim 4, wherein n=16.

6. The functional electrical stimulation system according to claim 1, further comprising an active discharge circuit;

wherein the central control unit is configured to generate an active discharge signal when the system is turned off, suspended or in an emergency stop state; and one end of the active discharge circuit is connected to the energy storage module and the other end is connected to the ground, to receive an active discharge signal to release the electrical energy stored in the energy storage module.

7. The functional electrical stimulation system according to claim 6, wherein the active discharge circuit comprises a third transistor, an eighth resistor and a ninth resistor;

wherein a collector of the third transistor is connected to the energy storage module via the eighth resistor, an emitter of the third transistor is connected to the ground, and a base of the third transistor is connected to the central control unit via the ninth resistor;

wherein, when the system operates in a normal mode, the third transistor is turned off; and wherein, when the system is turned off, suspended or in the emergency stop state, the active discharge signal is set to a high level by the central control unit to turn on the third transistor, and the electrical energy stored in the energy storage module is released via the eighth resistor.

8. The functional electrical stimulation system according to claim 1, further comprising:

an automatic discharge circuit having a control terminal connected or connectable to the primary power, and configured to release the electrical energy stored in the energy storage module when the output voltage of the primary power is lower than the first preset voltage.

9. The functional electrical stimulation system according to claim 8, wherein the automatic discharge circuit comprises a fourth transistor, a fifth transistor, a tenth resistor, an eleventh resistor, a twelfth resistor and a thirteenth resistor;

a base of the fourth transistor is connected to a primary power voltage signal via the thirteenth resistor, a collector of the fourth transistor is connected to the energy storage module via the tenth resistor, and an emitter of the fourth transistor is connected to the ground;

a base of the fifth transistor is connected to the collector of the fourth transistor via the eleventh resistor a collector of the fifth transistor is connected to the energy storage module via the twelfth resistor, and an emitter of the fifth transistor is connected to the ground;

wherein, when the output voltage of the primary power is higher than the first preset voltage, the fourth transistor is turned on and the fifth transistor is turned off; and wherein, when the output voltage of the primary power is lower than the first preset voltage, the fourth transistor is turned off and the fifth transistor is turned on so as to release the electrical energy stored in the energy storage module via the twelfth resistor.

10. The functional electrical stimulation system according to claim 1, further comprising:

a fuse connected between the energy storage module and the electrical stimulation output channel, the fuse configured to disconnect a connection between the energy storage module and the electrical stimulation output channel when a level of the current outputted from the energy storage module is higher than a first preset current value.

11. The functional electrical stimulation system according to claim 10, wherein the fuse is a 25 mA fast-blow fuse.

12. The functional electrical stimulation system according to claim 6, further comprising:

a voice-control emergency stop module configured to generate a voice-control emergency stop signal when a voice higher than a preset intensity or frequency is received;

wherein the central control unit is configured to generate the active discharge signal by the voice-control emergency stop signal; and the active discharge circuit is configured to receive the active discharge signal to release the electrical energy stored in the energy storage module.

13. The functional electrical stimulation system according to claim 12, wherein the central control unit is configured to generate an alarm signal by the voice-control emergency stop signal; and the functional electrical stimulation system further comprises an alarm circuit configured to receive the alarm signal to generate an audible and/or visual alarm signal.

14. The functional electrical stimulation system according to claim 1, further comprising;

a mechanical emergency stop module having a normally open contact connected between the energy storage module and the electrical stimulation output channel;

wherein the normally open contact is turned on when the functional electrical stimulation system is in a normal mode, and the normally open contact is turned off when an emergency occurs so that a pathway between the energy storage module and the electrical stimulation output channel is disconnected.

15. The functional electrical stimulation system according to claim 14, wherein the mechanical emergency stop module is a pressing-button switch;

wherein the normally open contact is turned on when a user is treading or pressing the switch in the normal mode, and the normally open contact is turned off when releasing the switch in an emergency.

16. The functional electrical stimulation system according to claim 15, further comprising:
an alarm circuit connected to the mechanical emergency stop module, the alarm circuit configured to generate an audible and/or visual alarm signal when the normally open contact is turned off.

17. The functional electrical stimulation system according to claim 1, further comprising:
a human-machine interaction module configured to receive the electrical stimulation parameters entered by the user,
wherein the central control unit is connected to the human-machine interaction module, and configured to generate the data packets of electrical stimulation parameters based on the electrical stimulation parameters entered by the user, and transmit the data packets of electrical stimulation parameters to the electrical stimulation output channel.

18. The functional electrical stimulation system according to claim 1, further comprising:
a communication interface module configured to receive the data packets of electrical stimulation parameters inputted from a user terminal,
wherein the central control unit is connected to the communication interface module, and configured to analyze the data packets of electrical stimulation parameters and package it into analyzable data packets of electrical stimulation parameters for the electrical stimulation output channel.

19. The functional electrical stimulation system according to claim 18, wherein the electrical stimulation parameters included in the data packets of electrical stimulation parameters outputted from the user terminal contain electrical stimulation waveform parameters obtained by modulating an audio signal, a real-time electromyographic signal for the user and/or a fixed waveform sequence.

20. The functional electrical stimulation system according to claim 18, wherein the communication interface module is a RS232 communication interface.

21. The functional electrical stimulation system according to claim 1, wherein parameters of the electrical stimulation output channel are set in a range of a positive pulse width of 0-1000 µs, a negative pulse width of 0-3000 µs, a positive pulse amplitude of 0-100 mA, a negative pulse amplitude 0-50 mA and a pulse frequency of 0-100 Hz.

22. The functional electrical stimulation system according to claim 1, wherein the primary power is a battery; the boost module is a DC boost module; and the energy storage module is a storage capacitor.

* * * * *